(12) United States Patent
Goldfarb et al.

(10) Patent No.: US 11,839,362 B2
(45) Date of Patent: Dec. 12, 2023

(54) VISUALIZATION DEVICES AND METHODS FOR OTOLOGIC PROCEDURES

(71) Applicant: TUSKER MEDICAL, INC., Menlo Park, CA (US)

(72) Inventors: Eric Goldfarb, Belmont, CA (US); Mahyar Z. Kermani, San Ramon, CA (US); Rohit Girotra, San Francisco, CA (US)

(73) Assignee: Tusker Medical, Inc., Menlo Park, CA (US)

(*) Notice: Subject to any disclaimer, the term of this patent is extended or adjusted under 35 U.S.C. 154(b) by 813 days.

(21) Appl. No.: 16/961,353

(22) PCT Filed: Jan. 15, 2019

(86) PCT No.: PCT/US2019/013568
§ 371 (c)(1),
(2) Date: Jul. 10, 2020

(87) PCT Pub. No.: WO2019/143587
PCT Pub. Date: Jul. 25, 2019

(65) Prior Publication Data
US 2020/0337544 A1    Oct. 29, 2020

Related U.S. Application Data

(60) Provisional application No. 62/617,951, filed on Jan. 16, 2018.

(51) Int. Cl.
*A61B 1/227* (2006.01)
*A61B 1/00* (2006.01)
(Continued)

(52) U.S. Cl.
CPC ............ *A61B 1/227* (2013.01); *A61B 1/0005* (2013.01); *A61B 1/00006* (2013.01);
(Continued)

(58) Field of Classification Search
CPC .................................................. A61B 17/227
See application file for complete search history.

(56) References Cited

U.S. PATENT DOCUMENTS

| 4,034,759 A | 7/1977 | Haerr |
|---|---|---|
| 4,159,719 A | 7/1979 | Haerr |

(Continued)

FOREIGN PATENT DOCUMENTS

| CN | 102122067 A | 7/2011 |
|---|---|---|
| CN | 105725955 A | 7/2016 |

(Continued)

OTHER PUBLICATIONS

Communication pursuant to Rules 161(1) and 162 EPC for EP 19703486.1 dated Sep. 3, 2020, 3 pages.
(Continued)

*Primary Examiner* — Tessa M Matthews
(74) *Attorney, Agent, or Firm* — Dickinson Wright PLLC

(57) ABSTRACT

Systems, apparatuses, and methods are described for providing visualization inside an ear of a subject before, during, or after an otologic procedure. An apparatus (100) includes a light source (140), a sensor (130), a processor (152, 170), and a display (154, 172, 972). The light source (140) can be configured to provide incident light to a target area (TM), and the sensor (130) can be configured to capture reflected light from the target area (TM) to generate image data based on the reflected light. The processor (152, 170) can process the image data to produce an image of the target area (TM), and the display (154, 172, 972) can display the image of the target area (TM).

20 Claims, 13 Drawing Sheets

(51) Int. Cl.
  *A61B 1/018* (2006.01)
  *A61B 1/04* (2006.01)
  *A61B 1/05* (2006.01)
  *A61B 1/06* (2006.01)
  *A61B 1/07* (2006.01)
  *A61B 1/32* (2006.01)

(52) U.S. Cl.
  CPC ........ *A61B 1/0014* (2013.01); *A61B 1/00048* (2013.01); *A61B 1/00052* (2013.01); *A61B 1/000094* (2022.02); *A61B 1/018* (2013.01); *A61B 1/042* (2013.01); *A61B 1/05* (2013.01); *A61B 1/0669* (2013.01); *A61B 1/0684* (2013.01); *A61B 1/07* (2013.01); *A61B 1/32* (2013.01)

(56) References Cited

U.S. PATENT DOCUMENTS

| | | | |
|---|---|---|---|
| 4,706,682 | A | 11/1987 | Stypulkowski et al. |
| 5,300,018 | A | 4/1994 | Walsh et al. |
| 5,489,286 | A | 2/1996 | Cinberg et al. |
| 5,954,682 | A | 9/1999 | Petrus |
| 6,045,528 | A | 4/2000 | Arenberg et al. |
| 6,120,484 | A | 9/2000 | Silverstein |
| 6,358,231 | B1 | 3/2002 | Schindler et al. |
| 6,685,697 | B1 | 2/2004 | Arenberg et al. |
| 8,052,693 | B2 | 11/2011 | Shahoian |
| 8,747,883 | B2 | 6/2014 | Labib et al. |
| 8,864,774 | B2 | 10/2014 | Liu et al. |
| 8,998,927 | B2 | 4/2015 | Kaplan et al. |
| 9,233,068 | B2 | 1/2016 | Lichter et al. |
| 9,320,652 | B2 | 4/2016 | Andreas et al. |
| 9,326,668 | B1 | 5/2016 | Berbee et al. |
| 9,370,448 | B2 | 6/2016 | Loushin et al. |
| 9,681,891 | B2 | 6/2017 | Andreas et al. |
| 9,833,360 | B2 | 12/2017 | Andreas et al. |
| 2010/0256653 | A1* | 10/2010 | Kaplan ............... A61B 90/37 606/109 |
| 2011/0208161 | A1 | 8/2011 | Ivri |
| 2012/0130252 | A1* | 5/2012 | Pohjanen ............. A61B 1/04 600/476 |
| 2012/0253267 | A1* | 10/2012 | Reed ................ A61M 1/774 604/28 |
| 2014/0276906 | A1 | 9/2014 | Andreas et al. |
| 2015/0293877 | A1 | 10/2015 | Liang et al. |
| 2016/0022497 | A1 | 1/2016 | Labib et al. |
| 2016/0038342 | A1 | 2/2016 | Van et al. |
| 2016/0067179 | A1 | 3/2016 | Lichter et al. |
| 2017/0172804 | A1 | 6/2017 | Watanabe et al. |
| 2017/0239091 | A1 | 8/2017 | Franz et al. |
| 2018/0125345 | A1 | 5/2018 | Rebella et al. |
| 2019/0167378 | A1 | 6/2019 | Wood et al. |
| 2021/0038234 | A1 | 2/2021 | Amis et al. |
| 2022/0240771 | A1 | 8/2022 | Domecus et al. |

FOREIGN PATENT DOCUMENTS

| | | | | |
|---|---|---|---|---|
| GB | 842965 | A | 8/1960 | |
| TW | 201200098 | A | 1/2012 | |
| WO | 0128407 | A1 | 4/2001 | |
| WO | 02056756 | A2 | 7/2002 | |
| WO | WO-02056756 | A2 * | 7/2002 | ......... A61B 1/00016 |
| WO | 2015168642 | A1 | 11/2015 | |

OTHER PUBLICATIONS

IPRP for PCT/US2019/013568 dated Jul. 21, 2020, 12 pages.
Patent Cooperation Treaty, Search Report and Written Opinion for International Application No. PCT/US2019/013568, dated Jun. 14, 2019; 18 pages.
Japanese Application No. 2020-536682 Notice of Reasons for Rejection dated Jan. 30, 2023.
International Search Report and Written Opinion dated Dec. 14, 2020 for International Application No. PCT/US2020/042484, 19 pages.
Chinese Application No. 201480006220.6 Text Of Decision Of Rejection.
European Application No. 19703486.1-1126 Examination Report dated May 24, 2023.

* cited by examiner

VISUALIZATION DEVICES AND METHODS FOR OTOLOGIC PROCEDURES

CROSS-REFERENCE TO RELATED APPLICATIONS

This application is a U.S. National Phase Entry of PCT application Ser. No. PCT/US2019/013568 filed Jan. 15, 2019 and titled "VISUALIZATION DEVICES AND METHODS FOR OTOLOGIC PROCEDURES." The PCT application claims priority to U.S. Provisional Patent App. No. 62/617,951, filed Jan. 16, 2018, titled "VISUALIZATION DEVICES AND METHODS FOR OTOLOGIC PROCEDURES." The PCT application and the provisional application are both incorporated by reference herein.

TECHNICAL FIELD

The present disclosure relates generally to systems, apparatuses, and methods for visualizing an ear of a subject during an otologic or in ear procedure. More specifically, the present disclosure relates to visualization devices including one or more cameras and lights for visualizing an interior of a subject's ear canal during a tympanostomy tube placement procedure.

BACKGROUND

Otologic procedures, or procedures relating to the ear, typically involve the insertion of a medical instrument into an ear of a subject. For example, otitis media is a common disease of the middle ear associated with inflammation. Otitis media is common in human children due to their anatomy and immune function. If severe or untreated, otitis media may result in rupture of an individual's tympanic membrane, hearing loss, or intracranial complications.

Treatment of otitis media may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane.

Insertion of a pressure equalization tube can be performed using a delivery device that can gain access to the tympanic membrane to perform a myringotomy procedure. The delivery device can include a cutting element that can create an opening or incision in the tympanic membrane. The pressure equalization tube then can be placed within the opening to provide fluid communication between the middle and outer ear. In some cases, iontophoresis can be used prior to performing the myringotomy procedure and tube placement to deliver local anesthetic to the tympanic membrane and surrounding tissues. Iontophoresis involves the application of a low-level electric current to a charged drug solution. The electric current repels similarly charged ions of the drug within the solution and transports them across the skin or other membrane. Iontophoresis can be performed using a device that can seal a charged drug solution within the ear canal while applying an electric current to the solution.

During an iontophoresis procedure and/or a tube placement procedure, as well as other otologic procedures, it may be difficult for a physician to view inside the ear. Otologic procedures are conventionally performed using a surgical microscope that provides visualization of the ear but requires a line-of-sight view to a target treatment area. When operating with an instrument within the ear canal, however, the access path of the instrument oftentimes overlaps or blocks the line of sight between the microscope and the target treatment area. Therefore, a physician may be restricted in his operation of the instrument or must operate with an incomplete view of the target treatment area. To avoid view interference, physicians have developed techniques to adjust instrument placement, but this can result in sub-optimal instrument positioning and add to the time to perform a procedure. Therefore, it is desirable to have a system for otologic procedures that allows instrument access to a target treatment area while providing a clear view of the target treatment area.

SUMMARY

Systems, apparatus, and methods are described for visualizing within an ear of a subject during an otologic procedure.

In some embodiments, an apparatus includes a light source, a sensor, a processor, and a display. The light source can be configured to provide incident light to a target area, and the sensor can be configured to capture reflected light from the target area to generate image data based on the reflected light. The processor can process the image data to produce an image of the target area, and the display can display the image of the target area.

In some embodiments, an apparatus includes a speculum where a sensor and/or a light source are disposed at a distal end of the speculum. In some embodiments, an apparatus includes a separate stylus having a sensor and/or a light source.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 9A provides a side view of the visualization system, and FIG. 9B provides a view from a distal end of the visualization system.

FIG. 10A provides a side view of the visualization system, and FIG. 10B provides a view from a distal end of the visualization system.

DETAILED DESCRIPTION

Systems, apparatuses, and methods are described herein for visualizing within an ear of a subject during an otologic procedure. In some embodiments, systems, apparatuses, and methods described herein can be used to provide visualization within the ear before, during, or after a pressure equalization or tympanostomy tube placement procedure.

Figure 1:
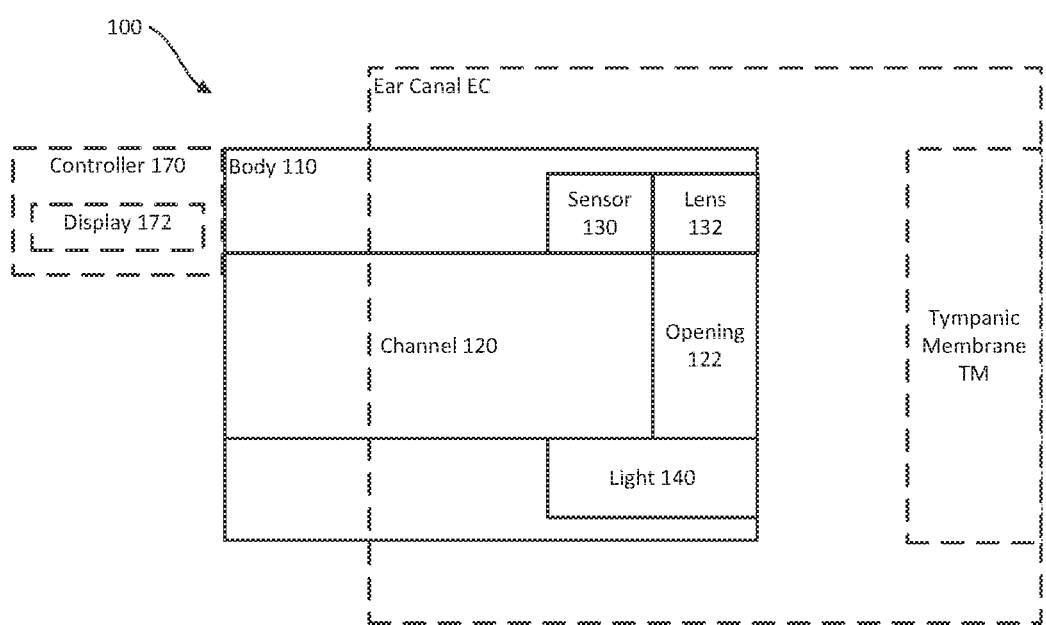
FIG. 1 is a schematic illustration of a visualization system according to some embodiments.

As illustrated schematically in FIG. 1, an example visualization system including a guide device 100 can be positioned in an ear canal EC of a subject and provide a view of a target treatment area such as a tympanic membrane TM. Guide device 100 can be configured to guide an instrument into ear canal EC. In an embodiment, guide device 100 can be shaped and function similar to a speculum. Guide device 100 includes a body 110 that defines a channel or lumen 120 for receiving an instrument. Channel 120 can terminate in an opening 122 at a distal end of the body 110 positioned within ear canal EC. An instrument, such as a tube delivery device, can be inserted through channel 120 and out through opening 122 into ear canal EC. Channel 120 can have a tapered shape that gradually decreases in diameter from the proximal end to the distal end of body 110 (e.g., as in a speculum), or have a fixed diameter.

Guide device 100 can be anatomically sized to fit within ear canal EC. For example, guide device 100 can be available in a number of different sizes, e.g., with opening 122 of guide device 100 being 4 millimeters (mm), 4.5 mm, 5 mm, 6 mm, 7 mm, or any other size within those sizes. Guide device 100 can be designed for single use or be reusable.

Guide device 100 includes a sensor 130 and a light 140. Sensor 130 can be a light sensor, a pressure sensor, a temperature sensor, or any other type of sensor capable of capturing information about a target treatment area. In an embodiment, sensor 130 is an image sensor such as a complementary metal oxide semiconductor (CMOS) sensor or a charge-coupled device (CCD) sensor. Sensor 130 can be dimensioned such that it can be embedded within a wall of body 110. Alternatively, sensor 130 can be disposed on an exterior or interior surface of body 110. In an embodiment, sensor 130 can be approximately 0.5 mm to 1 mm in width and 0.5 mm to 1 mm in length. Sensor 130 can provide high resolution. For example, sensor 130 can have a pixel resolution of 40,000 to 160,000 pixels. Sensor 130 can be capable of operating under low light conditions. In some embodiments, sensor 130 can have a field of view of 90 to 120 degrees. In some embodiments, sensor 130 can have a depth of focus of 5 mm to 30 mm. In some embodiments, sensor 130 can have a frame rate for enabling video capture, such as, for example, a frame rate of at least 16 frames per second. A low-level power source, such as a battery, can be used to power sensor 130.

Sensor 130 can produce an analog output, e.g., sensor 130 can produce a charge that is proportional to an amount of light that is captured by sensor 130. Sensor 130 can provide this analog output to separate processing circuitry or a compute device for additional processing. The processing circuitry or compute device can be coupled to sensor 130 via wires, couplers, etc. With this arrangement, fewer components are placed at the distal end of body 110, thereby reducing the size of the components that need to be placed at the distal end of body 110 and/or integrated into a wall of body 110. This reduction in the size can provide greater clearance for an instrument to be inserted through opening 122 into ear canal EC.

Figure 5:
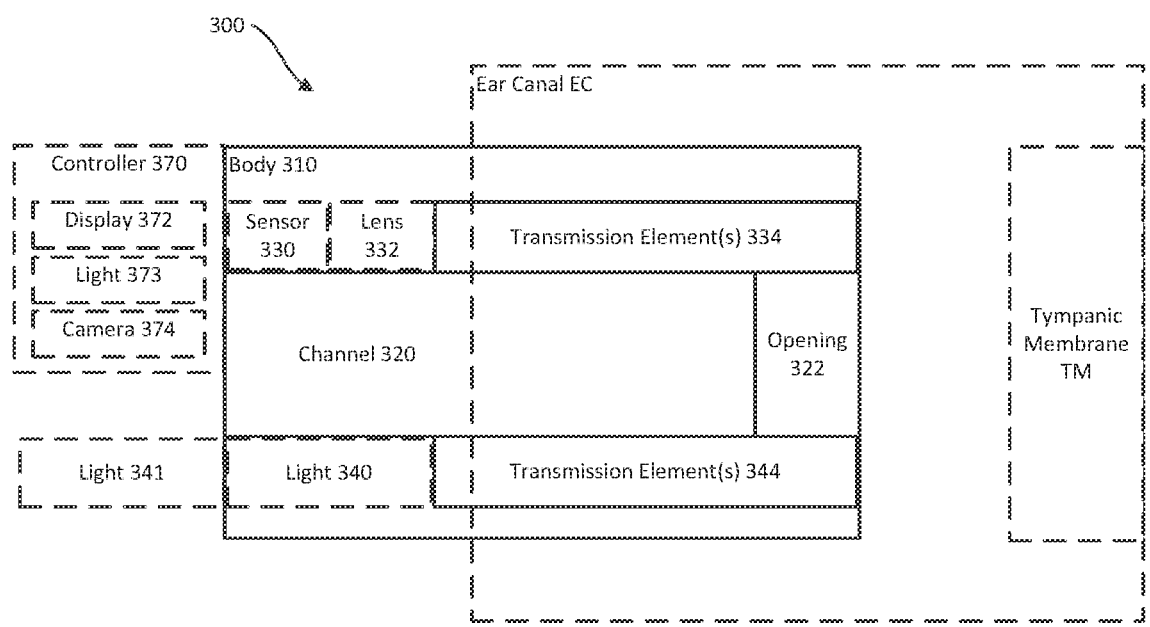
FIG. 5 is a schematic illustration of a visualization system according to some embodiments.

In some embodiments, such as the embodiment shown in FIG. 5, sensor 130 can be positioned at a proximal end of body 110. By moving sensor 130 to the proximal end of body 110, the size of components at the distal end of body 110 can be further reduced. In such embodiments, optical fibers or another transmission element (e.g., a wire or cable) can be used to transmit light or image data from the distal end of body 110 to sensor 130. Multiple optical fibers can be bundled together to increase performance. But the resolution of the transmitted image may be limited by the number of fibers that can be bundled together, which can be restricted by the size of guide device 100. In general, the number of fibers in a small bundle can range from 4,000 to 8,000 fibers. The optical fibers may also require a greater amount of light in order to provide adequate image transfer. Accordingly, it may be advantageous to dispose sensor 130 at the distal end of body 110.

Guide device 100 also includes a lens 132 that can be used to focus light that is captured by sensor 130. Lens 132 can be integrated with sensor 130. In some embodiments, sensor 130 with integrated lens 132 can be mounted on an integrated circuit or chip, which can be attached to the distal end of body 110. The integrated circuit or chip can be flexible such that it can be easily mounted to the distal end of body 110. In some embodiments, lens 132 can be separately assembled from sensor 130 to provide additional visualization performance, such as, for example, higher resolution, different field of view or depth of focus, etc. In some embodiments, visualization device 100 may allow a user to adjust a focus length of lens 132 to change performance. In some embodiments, lens 132 can also be designed to filter for specific colors of light, such as, for example, when it may be desirable to identify sensitive anatomical regions (e.g., thinner tissue areas) and areas that have become blanched due to an interaction with a drug (e.g., blanching from absorption of epinephrine).

Light 140 can deliver light to ear canal EC and tympanic membrane TM. Light 140 can be disposed at the distal end of body 110, e.g., light 140 can be integrated into the distal end of body 110. Light 140 can be a small, high intensity, light-emitting diode (LED). In some embodiments, multiple lights 140 can be integrated into and/or mounted to the distal end of body 110.

Alternatively or additionally, light can be provided to ear canal EC by a separate light source (not depicted), e.g., a light source in a procedure room, a light source from a mobile device or other portable device, or a light source worn by a physician such as a headlamp. The light source can flood the area near the opening of the ear with light, and the light can be transmitted to the distal end of body 110 via a light cable, light tube, or other transmission element. In some embodiments, one or more couplers can be used to connect the light source to the transmission element such that the light from the light source 100 can be directed into the transmission element. An example of such a light arrangement is depicted in FIG. 5, and further details of that example are provided below with reference to FIG. 5.

Guide device 100 can optionally be coupled to a controller 170. Controller 170 can optionally include a display 172. Controller 170 can be powered by a battery or other portable power source. Controller 170 can be coupled to and/or integrally formed as a part of body 110. Display 172 can display images of the target treatment area including tympanic membrane TM. In some embodiments, display 172 can display a real-time view of the target treatment area. Controller 170 and display 172 can be disposed adjacent to guide device 100 such that an in-ear view from the display 172 and a physician's actual view of the ear are in the same field. Image data from sensor 130 can be transmitted via a wire (not depicted) or wirelessly via Bluetooth, WiFi, or other wireless transmission means to controller 170, which can process the image data for display on display 172.

Figure 2:
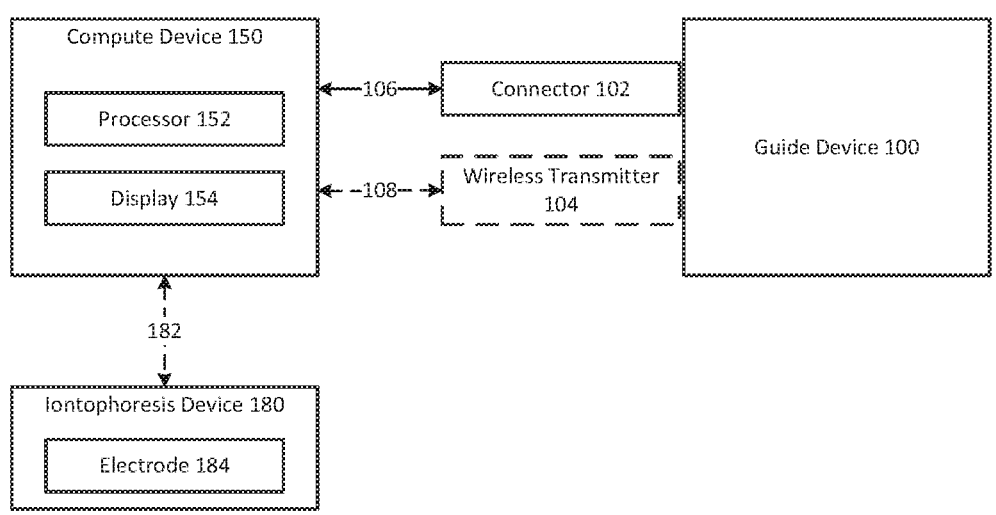
FIG. 2 is a schematic illustration of the visualization system depicted in FIG. 1 connected to a compute device having a display according to some embodiments.

In some embodiments, controller 170 can be configured to supply power to an iontophoresis device (e.g., iontophoresis device 180 in FIG. 2). The iontophoresis device can be integrated into the visualization system and/or controller 170 can be coupled to iontophoresis device such that controller 170 can activate an electrode of the iontophoresis device to supply current to an iontophoresis solution. For example, components of an iontophoresis device (e.g., electrode, circuitry for controlling the iontophoresis, etc.) can be integrated into the visualization system and controller 170 can be used to control and supply power the iontophoresis device. Alternatively, controller 170 can be removably coupled to an iontophoresis device via a wire or cable. Controller 170 can include a button, switch, or other actuation mechanism that can be actuated to activate the electrode. In some embodiments, display 172 can be a touch sensitive display that can display one or more graphical user interface elements (e.g., buttons, scales, bars, panels) that can be manipulated by a physician to activate and control delivery of electric current. Controller 170 can monitor the electric current that is delivered via the iontophoresis device and automatically stop the electric current when the iontophoresis process is completed and/or when it detects a safety issue. For example, controller 170 can receive data from sensor 130 and/or other sensors (e.g., light sensors, temperature sensors, pressure sensors, etc.) that are located on guide device 100 or the iontophoresis device and monitor the data for abnormalities (e.g., temperature increase, pressure increase, etc.). In some embodiments, controller 170 can be designed for single use. For example, controller 170 can be equipped with a battery or other portable power source that has sufficient charge to power a single iontophoresis procedure and display 172 before and during the iontophoresis procedure and subsequent tube delivery procedure.

In some embodiments, guide device 100 can be connected to a separate compute device 150, as schematically shown in FIG. 2. Guide device 100 can be connected via a connector 102 (e.g., a wire or cable) to compute device 150, as represented by connection 106. Alternatively or additionally, guide device 100 can be coupled to a wireless transmitter 104 that can wirelessly communicate information to compute device 150, as represented by connection 108. Guide device 100 can be powered via connection 106, or in the wireless configuration, guide device 100 can have an onboard battery or other portable power source for providing power to guide device 100 (e.g., a portable power source of controller 170). Guide device 100, via connections 106 and/or 108, can transmit image data from sensor 130, as well as data from any other sensors (not depicted) coupled to guide device 100, to compute device 150. Compute device 150 can be a desktop computer, a laptop, a tablet, a mobile or portable device, a smartphone, or any other type of device having computing capabilities. In some embodiments, compute device 150 can be a wearable display, such as, for example, GoogleGlass™.

Compute device 150 includes a processor 152 and a display 154. Processor 152 can be configured to process the image data from sensor 130 to produce images of the target treatment area for display on display 154. Display 154 can be positioned within the physician's field of view during an otologic procedure such that the physician can view display 154 and the ear in the same field. A physician can adjust the view from display 154 (e.g., by rotating guide device 100 and/or moving sensor 130) and his hand and/or instrument position separately to gain a clear view of the target treatment area during an otologic procedure. In some embodiments, processor 152 can be configured to filter the image data to selectively view different structures and physiological conditions. For example, similar to lens 132, processor 152 can be configured to digitally filter for wavelengths of light to identify sensitive anatomical regions (e.g., thinner tissue areas) and areas that have become blanched due to an interaction with a drug (e.g., blanching from absorption of epinephrine). In some embodiments, processor 152 can be configured to enhance visualization of the target treatment area by changing the light intensity of light 140 and/or other light sources (e.g., auto-dim light 140 when there is image saturation), auto-focusing lens 132 to select a desired focal point, filtering out noise, enhancing edges and sharpening, rotating the mage, etc.

In some embodiments, one or more of sensor 130, lens 132, and light 140 can be movable on guide device 100. For example, sensor 130 and lens 132 can be designed to rotate on guide device 100. When sensor 130 and lens 132 are rotated, compute device 150 via processor 152 can be configured to rotate the image of the target treatment region such that the image orientation presented to the physician does not change. A gyroscope, accelerometer or other type of motion sensor (not depicted) can be coupled to sensor 130 and/or lens 132 to sense the rotation of sensor 130 and/or lens 132. Data from the gyroscope can be transmitted to compute device 150, via connections 106 and/or 108, and processor 152 can rely on the data to determine when to auto-rotate the image of the target treatment area on display 154.

In some embodiments, compute device 150 can receive image data from multiple image sensors, including image sensor 130. For example, additional image sensors can be coupled to body 110 of guide device 100, or other devices inserted within ear canal EC (e.g., an iontophoresis device, a tube delivery device, a stylus), and the image data from these additional image sensors can be sent via one or more connections to compute device 150. Compute device 150, upon receiving the image data, create different views of the target treatment region. For example, compute device 150, via display 154, can create a binocular view, toggle between different sensors and cameras, construct a larger or clearer view of ear canal EC using the image data, or display multiple views simultaneously (e.g., side-by-side or picture-in-picture).

In some embodiments, compute device 150 can visually identify regions of interest in the displayed images on display 154. For example, compute device 150 via processor 152 can identify a target location for placement of a tympanostomy tube. Alternatively or additionally, compute device 150 can highlight areas of sensitive anatomy to avoid (e.g., an anterior overhang, a region of thin tissue) when performing an otologic procedure such as a tube delivery procedure.

In some embodiments, compute device 150 can be configured to store images and/or videos of a target treatment region. Stored images and/or videos can later be reviewed by a physician to assess an issue or, if used in a training setting, as an educational tool.

Optionally, compute device 150 can also be connected to an iontophoresis device 180, as represented by optional connection 182. Iontophoresis device 180 can form a part of the visualization system (i.e., be integrated into guide device 100 or other component(s) of the visualization system), or iontophoresis device 180 can be a separate device that is removably coupleable to compute device 150. Iontophoresis device 180 can be configured to perform an iontophoresis procedure. Iontophoresis device 180 can include an electrode 184 for supplying an electric current to an iontophoresis solution. Examples of iontophoresis systems are disclosed in U.S. Pat. No. 8,452,392, titled "Systems and Methods for Anesthetizing Ear Tissue," issued May 27, 2013; U.S. Pat. No. 8,840,602, titled "Systems and Methods for Anesthetizing Ear Tissue," issued Sep. 23, 2014; and U.S. Patent Application Publication No. 2017/0014272, titled "Earplug Assembly for Iontophoresis System," published Jan. 19, 2017. The disclosure of each of these references is incorporated herein by reference.

Compute device 150 can be configured to supply power to iontophoresis device 180 to activate electrode 184. Similar to controller 170, compute device 150 can include a button, switch, or other actuation mechanism that can be actuated to activate the electrode. In some embodiments, display 154 can be a touch sensitive display that can display one or more graphical user interface elements (e.g., buttons, scales, bars, panels) that can be manipulated by a physician to activate and control delivery of electric current. Compute device 150 can monitor the electric current that is delivered via the iontophoresis device and automatically stop the electric current when the iontophoresis process is completed and/or when it detects a safety issue. For example, compute device 150 can receive data from sensor 130 and/or other sensors (e.g., light sensors, temperature sensors, pressure sensors, etc.) that are located on guide device 100 or the iontophoresis device and monitor the data for abnormalities (e.g., temperature increase, pressure increase, etc.).

Figure 3:
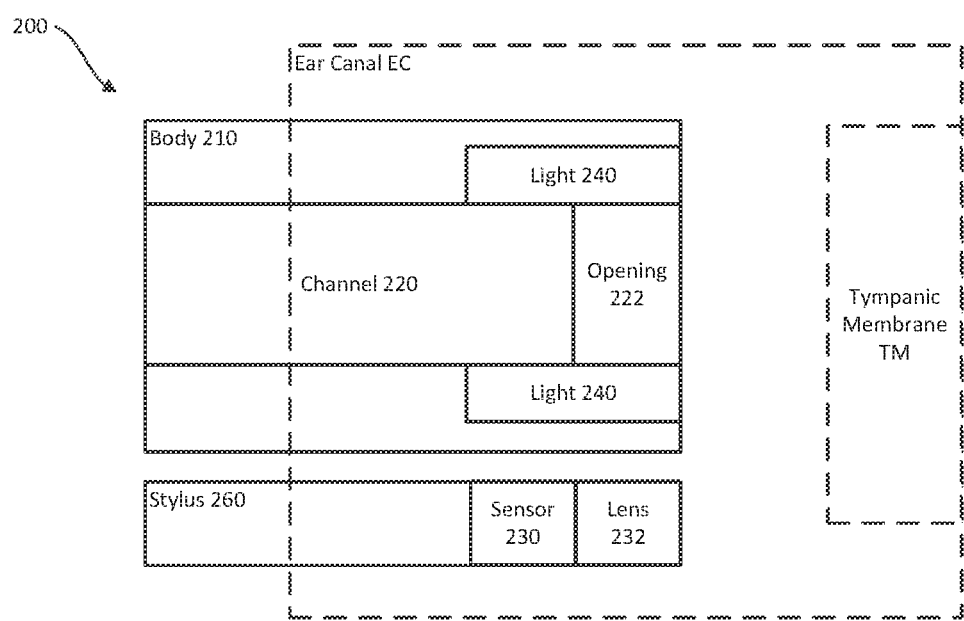
FIG. 3 is a schematic illustration of a visualization system including a stylus according to some embodiments.

FIG. 3 schematically illustrates another example of a visualization system, including a guide device 200 and a stylus 260. Guide device 200 is similar to guide device 100 but does not include a sensor at its distal end. Without a sensor at the distal end, guide device 200 has more space for light transmission elements (e.g., optical fibers, lights, etc.). In an embodiment, guide device 200 can be a speculum. Guide device 200 includes a body 210 that defines a channel 220 and an opening 222 for receiving an instrument and guiding the instrument into ear canal EC. The instrument can be, for example, a tympanostomy tube delivery device, such as tube delivery device 290 depicted in FIG. 4.

Guide device 200 includes one or more lights 240 that can deliver light to ear canal EC and tympanic membrane TM. Light 240 can be disposed at the distal end of body 110, e.g., light 240 can be integrated into the distal end of body 210. In an embodiment, light 240 can be a LED.

Stylus 260 includes a sensor 230 and a lens 232. Stylus 260 can be removably coupleable to an instrument that is inserted into ear canal EC via channel 220 and opening 222. For example, stylus 260 can be coupleable to a shaft of a tube delivery device (e.g., tube delivery device 290). Stylus 260 can be coupled to the shaft of the tube delivery device via an adhesive or tape, a mechanical fastener, or magnetically. Stylus 260 can be designed to have a small profile (e.g., approximately 1.5 mm to 3 mm in diameter) such that it does not interfere with the insertion of instrument into ear canal EC. Alternatively, in some embodiments, stylus 260 can be coupled to guide device 200.

Sensor 230 can be disposed at a distal end of stylus 260. Sensor 230 can be embedded into a wall of stylus 260, or sensor 230 can be disposed on a surface of stylus 260. Similar to sensor 130, sensor 230 can be an image sensor such as a CMOS or CCD sensor. Sensor 230 can be similarly dimensioned and provide similar resolution, field of view, depth of focus, and frame rate as sensor 130. Sensor 230 can produce an analog output (e.g. a charge proportional to an amount of light that is captured by sensor 230) that is provided to separate processing circuitry or a compute device for additional processing. The processing circuitry or compute device can be coupled to stylus 260 and sensor 230 via wires, couplers, etc. With this arrangement, fewer components are placed at the distal end of stylus 260, thereby reducing the size of the components that need to be placed at the distal end of stylus 260.

Lens 232 can be similar to lens 132 and can be used to focus light that is captured by sensor 230. Lens 232 can be integrated with sensor 230, or lens 232 can be a separate component from sensor 230. Both sensor 230 and lens 232 can be mounted on an integrated circuit. In some embodiments, lens 232 can be configured to filter for specific frequencies or colors of light for identifying areas of interest (e.g., sensitive anatomical regions, blanched tissue).

Figure 4:
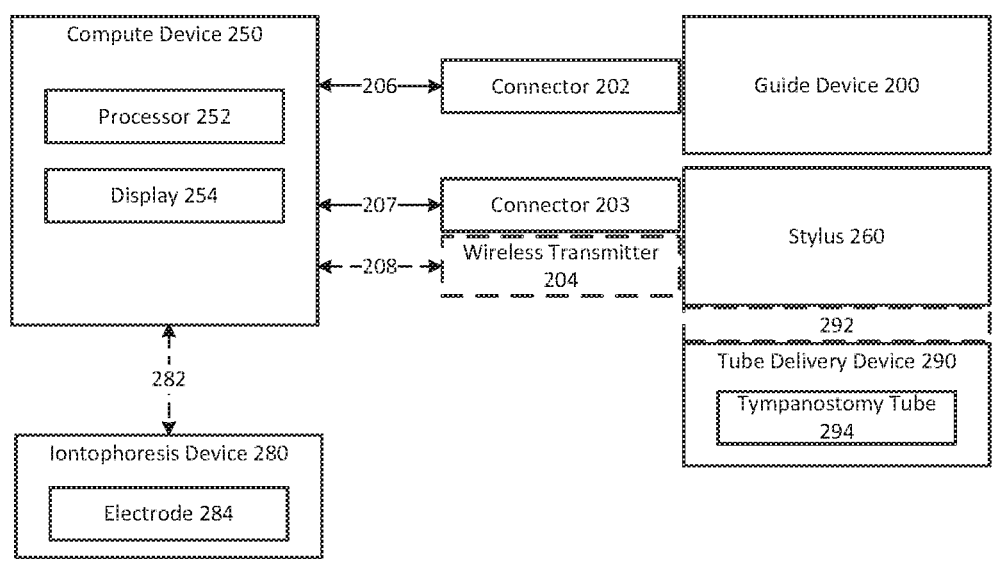
FIG. 4 is a schematic illustration of the visualization system depicted in FIG. 3 connected to a compute device and a tube delivery device according to some embodiments.

FIG. 4 schematically depicts connections between guide device 200 and stylus 260 and one or more other devices. Similar to guide device 100, guide device 200 can be connected via a connector 202 (e.g., a wire or cable) to a compute device 250, as represented by connection 206. Stylus 260 can be connected via a connector 203 (e.g., a wire or cable) to compute device 250, as represented by connection 207. Alternatively or additionally, stylus 260 can be coupled to a wireless transmitter 204 that can wirelessly communicate information to compute device 250, as represented by connection 208. Stylus 260 can be powered via connection 207, or in the wireless configuration, stylus 260 can have an onboard battery or other portable power source that can power stylus 260. If stylus 260 is powered via an onboard battery, compute device 250 (or a separate device) can include a docking station for recharging stylus 260. Stylus 260, via connections 207 and/or 208, can transmit image data from sensor 230 to compute device 250, which can be a desktop computer, a laptop, a tablet, a mobile or portable device, a smartphone, or any other type of device having computing capabilities. In some embodiments, stylus 260 can be connected to a different compute device (not depicted) than compute device 250 such that guide device 100 and stylus 260 are connected to different compute devices.

Stylus 260 can be coupled to a tube delivery device 290 via a coupling 292 (e.g., a mechanical or magnetic coupling). Tube delivery device 290 carries a tympanostomy tube 294 and is configured to place tympanostomy tube 294 in tympanic membrane TM. Examples of tympanostomy tube delivery systems are disclosed in U.S. Pat. No. 8,052, 693, titled "System and Method for the Simultaneous Automated Bilateral Delivery of Pressure Equalization Tubes," issued Nov. 8, 2011; U.S. Pat. No. 8,864,774, titled "Tympanic Membrane Pressure Equalization Tube Delivery System," issued Oct. 21, 2014; U.S. Pat. No. 9,320,652, titled "Features to Improve and Sense Tympanic Membrane Apposition by Tympanostomy Tube Delivery Instrument," issued Apr. 26, 2016; U.S. Pat. No. 9,681,891, titled "Tympanostomy Tube Delivery Device with Cutting Dilator," issued Jun. 20, 2017; U.S. Patent Application Publication No. 2016/0038342, titled "Tympanostomy Tube Delivery Device with Rotatable Flexible Shaft," published Feb. 11, 2016; and U.S. Pat. No. 9,833,360, titled "Tympanostomy Tube Delivery Device with Replaceable Shaft Portion," issued Dec. 5, 2017. The disclosure of each of these references is incorporated herein by reference.

Compute device 250 includes a processor 252 and a display 254. Processor 252 can be similar to processor 152. For example, processor 262 can be configured to process image data from sensor 230 to produce images of the target treatment area for display on display 254. In some embodiments, processor 252 can be configured to filter image data, enhance visualization of a target treatment area (e.g., via auto-dimming or auto-focusing, and/or via data processing algorithms), visually identify regions of interest (e.g., a target location for placement of tympanostomy tube 294, or sensitive anatomy to avoid), store images, etc.

In some embodiments, a sensor (not depicted) can be provided at the distal end of guide device 200 in addition to sensor 230 provided at the distal end of stylus 260. In such cases, processor 252 can be configured to toggle the view between that provided by the sensor located on guide device 200 and that provided by sensor 230. The view provided by the sensor located on guide device 200 can be an angled view of the target treatment region, and the view provided by sensor 230 can be an axial view down a length of an instrument to which stylus 260 is coupled (e.g., such as the example view shown in FIG. 13, further described below).

Optionally, compute device 250 can also be connected to an iontophoresis device 280, as represented by optional connection 282. Iontophoresis device 280 can be configured to perform an iontophoresis procedure. Iontophoresis device 280 can include an electrode 284 for supplying an electric current to an iontophoresis solution. Compute device 250 can be configured to activate electrode 284.

FIG. 5 schematically depicts another example of a visualization device, including a guide device 300. Similar to guide devices 100 and 200, guide device 300 includes a body 310 that defines a channel 320 and an opening 322 for receiving an instrument and guiding the instrument into ear canal EC. In an embodiment, guide device 300 can be a speculum. The instrument can be, for example, a tympanostomy tube delivery device.

Guide device 300 can optionally include a sensor 330 and a lens 332 that are located at a proximal end of body 310. Similar to sensors 130 and 230, sensor 330 can be an image sensor such as a CMOS or CCD sensor. Sensor 330 can be embedded into a wall of body 310, or sensor 330 can be disposed on a surface of body 310. Sensor 330 can be similarly dimensioned and provide similar resolution, field of view, depth of focus, and frame rate as sensors 130 and 230. Sensor 330 can produce an analog output (e.g. a charge proportional to an amount of light that is captured by sensor 330) that is provided to separate processing circuitry or a compute device for additional processing. The processing circuitry or compute device can be coupled to stylus 260 and sensor 230 via wires, couplers, etc. With this arrangement, fewer components are placed on and/or integrated into guide device 300, thereby reducing the weight of guide device 300 and/or the dimensions of guide device 300.

Guide device 300 includes one or more transmission elements 334, such as optical fibers or another transmission means (e.g., a wire or cable), which can be used to transmit light or image data from a distal end of body 310 to sensor 320. In the case of optical fibers, multiple optical fibers can be bundled together to increase performance. Light transmitted by optical fibers may also degrade over the length of the optical fibers; therefore, more light may be required to render a clear image of a target treatment area when compared to a guide device having sensor 330 at its distal end (e.g., guide device 100). But optical fibers or other transmission means can be smaller in size than sensor 320 and therefore reduce the size of the components coupled and/or integrated into the distal end of guide device 300. This can provide greater clearance for an instrument through opening 322.

Lens 332 can be similar to lenses 132 and 232 and can be used to focus light that is captured by sensor 330. Lens 332 can be integrated with sensor 330, or lens 332 can be a separate component from sensor 330. Both sensor 330 and lens 332 can be mounted on an integrated circuit. In some embodiments, lens 332 can be configured to filter for specific frequencies or colors of light for identifying areas of interest (e.g., sensitive anatomical regions, blanched tissue).

Guide device 300 can optionally include a light 340 for providing light to ear canal EC and tympanic membrane TM. Light 340 can be disposed at and coupled and/or integrated into the proximal end of body 310. Light 340 can be a LED or other type of light source. Alternatively or additionally, a light 341 that is separate from guide device 300 can be used to provide light to ear canal EC. For example, light 341 can be a light source in a procedure room or a light source worn by a physician (e.g., a headlamp). Light 341 can flood the area near the opening of ear canal EC with light. Light from lights 340 and/or 341 can be transmitted to the distal end of body 310 via a transmission element 344 (e.g., light cable, light tube). In some embodiments, one or more couplers (not depicted) can be used to couple light 341 to light transmission element 344 and to direct light from the light 341 into light transmission element 344.

Guide device 300 can optionally be coupled to a controller 370. Controller 370 can be similar to controller 170 and can optionally include a display 372, a light 373, and/or a camera 374. Controller 370 can be powered by a battery or other portable power source. Controller 370 can be coupled to and/or integrally formed as a part of body 310. Display 372 can display images of the target treatment area including tympanic membrane TM. In some embodiments, controller 370 can be configured to supply power to an iontophoresis device (e.g., iontophoresis device 180 in FIG. 2), similar to controller 170.

In an embodiment, controller 370 can be a mobile device. Mobile device can be coupled to guide device 300 via a specialized case (not depicted). The specialized case can include image couplers and light transmission elements, e.g., light transmission elements 334 and 344. Light (e.g., light 373) from the mobile device can be transmitted via the couplers and transmission element 344 to ear canal EC, and light from within ear canal EC can be transmitted to the mobile device via transmission element 334 such that a camera (e.g., camera 374) on the mobile device can capture images of ear canal EC. The mobile device can process the images captured by the camera and display the images for viewing by a physician. In this arrangement, guide device 300 functions as a passive element, and is used to transmit light from the mobile device and to return light from ear canal EC to the mobile device. The mobile device and specialized case can be disposed adjacent to the speculum or be positioned near the speculum, such as, for example, mounted on a head of a subject, or an arm of a physician, to enable the physician to view the images displayed on the mobile device in the same field of view of the ear of a subject before, during, or after an otologic procedure.

Figure 6:
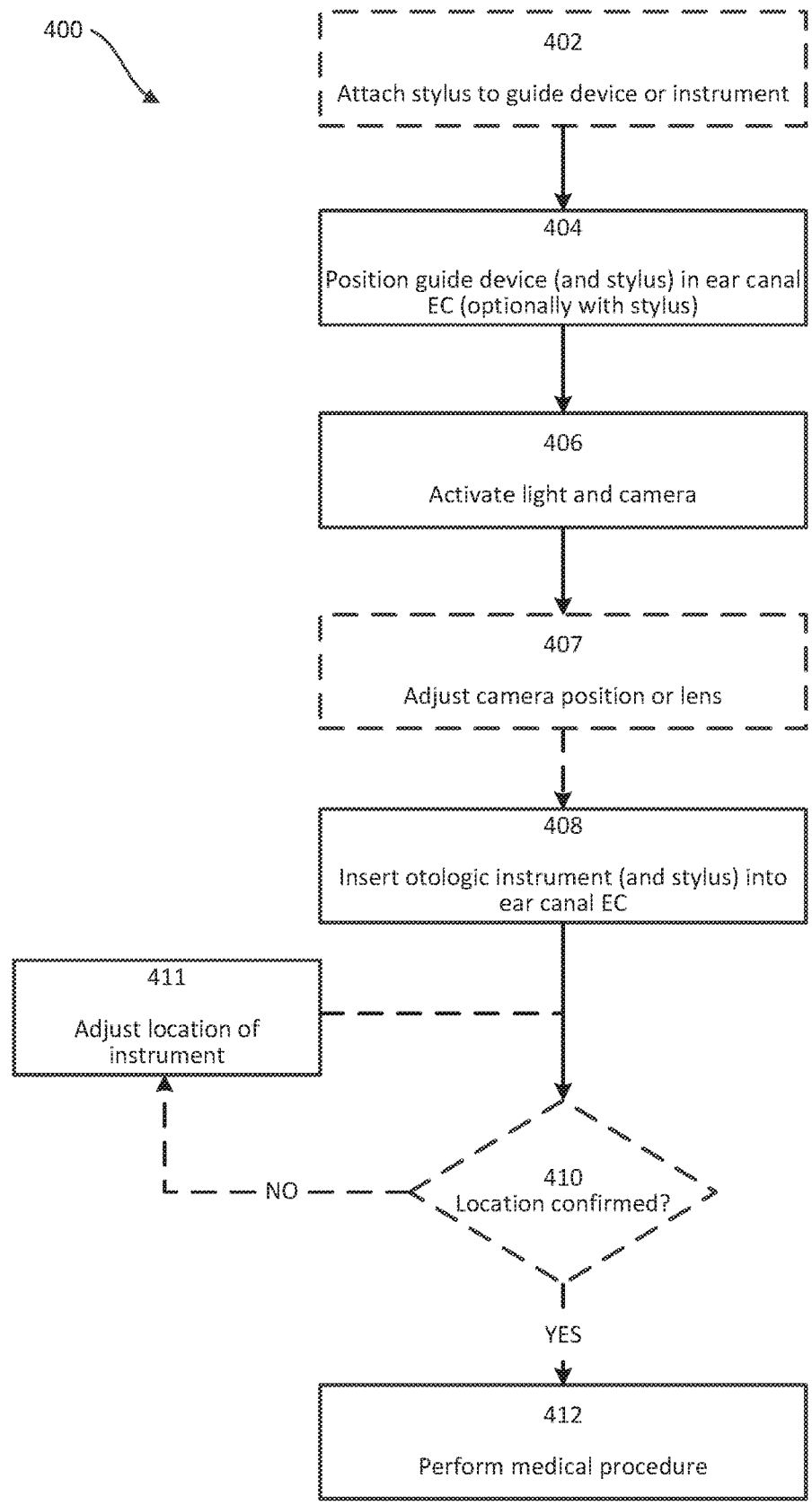
FIG. 6 is a flow diagram illustrating a method of using a visualization system according to some embodiments.

FIG. 6 is a flow diagram of a method 400 of using a visualization system, such as any of the visualization systems described herein. Method 400 can optionally include attaching a stylus (e.g., stylus 260) to a guide device or instrument, at 402. For example, a stylus can include a sensor or camera that can be used to capture image data of a target treatment area. In some embodiments, a stylus can include other sensors (e.g., a temperature sensor, a pressure sensor, etc.) that can be used to capture other data associated with a target treatment area.

At 404, the guide device (e.g., guide device 100, 200, or 300) and the stylus, if coupled to the guide device, can be positioned in an ear canal EC of a subject. The guide device can define a lumen or channel (e.g., channel 120, 220, or 320) for receiving and guiding an instrument into ear canal EC. The guide device and/or stylus can have one or more cameras or light sensors (e.g., sensors 130, 230, or 330), and lenses associated with the cameras or light sensors (e.g., lenses 132, 232, or 332). The guide device and/or stylus can also have one or more light sources (e.g., lights 140, 240, or 340). Alternatively or additionally, a separate light source (e.g., light 341) can be provided in a procedure room. The light sources and cameras can be activated, at 406, to provide a view of a target treatment region in ear canal EC on one or more displays (e.g., displays 172, 154, 254, or 372).

Depending on the provided view, the lenses and/or camera positions can optionally be adjusted, at 407, to improve the view of the target treatment region. The adjustments can be automatically controlled by a controller or compute device (e.g., controllers 170 or 370, or compute devices 150 or 250), or the adjustments can be manually made by a physician.

At 408, an otologic instrument (e.g., tube delivery device 290) and the stylus, if coupled to the otologic instrument, can be inserted into ear canal EC. Otologic instrument can be inserted through the lumen or channel defined by the guide device into ear canal EC. In some embodiments, otologic instrument can be inserted into the guide device before lights and cameras are activated, at 406, or adjustments are made to the cameras and/or lenses, at 407, i.e., step 408 may occur before steps 406 and 407.

The location of the otologic instrument can be confirmed, at 410. For example, a physician can view on the one or more displays the target treatment region and the position of the instrument relative to the target treatment region and, if needed, make adjustments to the position of the instrument, at 411, until the instrument is properly positioned to perform a medical procedure (e.g., delivery of a tympanostomy tube), at 412. The physician can adjust the instrument position without compromising the view that is provided by the cameras and lenses given the positioning of the cameras and lenses within ear canal EC, as described above with reference to the visualization systems depicted in FIGS. 1-5. This arrangement allows the physician to perform the medical procedure without relying on his line of sight of ear canal EC and the target treatment area, directly or via a microscope. In some embodiments, a physician can use the display to confirm successful completion of a medical procedure (e.g., delivery of a tympanostomy tube) after performing the medical procedure.

Figure 7:
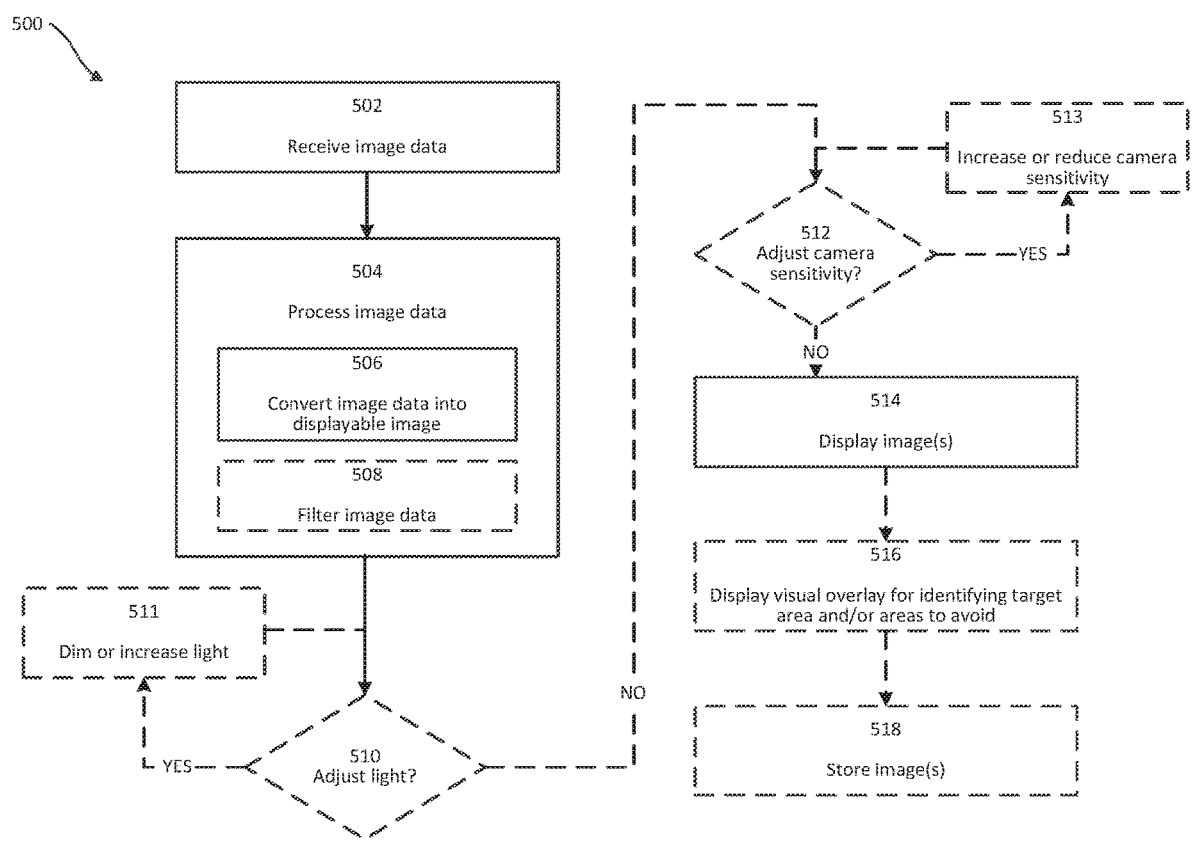
FIG. 7 is a flow diagram illustrating a method performed by a visualization system according to some embodiments.

FIG. 7 is a flow diagram of a method 500 performed by a visualization system, such as any of the visualization systems described herein. The visualization system can receive image data, at 502. The image data can come from one or more sensors (e.g., sensors 130, 230, or 330) located on a guide device (e.g., guide device 100, 200, or 300) or a stylus (e.g., stylus 260) that has been inserted into an ear canal EC. At 504, visualization system processes the image data. Visualization system can convert the image data into displayable image(s) of ear canal EC and a target treatment region, at 506. Visualization system, optionally, can also filter the image data, at 508. For example, visualization system can digitally filter for wavelengths of light to identify sensitive anatomical regions (e.g., thinner tissue areas) and areas that have become blanched due to an interaction with a drug (e.g., blanching from absorption of epinephrine).

At 510, the visualization system can optionally determine whether adjustments need to be made to light sources (e.g., lights 140, 240, 340, or 341) to improve image quality. For example, visualization system may determine that a clearer view of the target treatment region can be provided by increasing or decreasing light delivered into ear canal EC. Based on this determination, visualization system can auto-adjust the amount of light that is delivered into ear canal EC by increasing or dimming the light sources, at 511. Visualization system, optionally, can also determine whether camera sensitivity may need to be adjusted to improve image quality, at 512, and based on that determination, increase or reduce camera sensitivity, at 513.

At 514, the visualization system can display on a display (e.g., displays 172, 154, 254, or 372) the image(s) of ear canal EC and the target treatment region. Optionally, visualization system can also display a visual overlay on top of the image(s) of ear canal EC and target treatment region, at 516, to identify a target location for placement of a tympanostomy tube and/or highlight areas of sensitive anatomy to avoid (e.g., an anterior overhang, a region of thin tissue). Optionally, the visualization system can store the image(s) of ear canal EC and the target treatment region for future reference, at 518. Visualization system can store the image(s) on a local memory or transmit them via a network to a device or server for storage.

Figure 8:
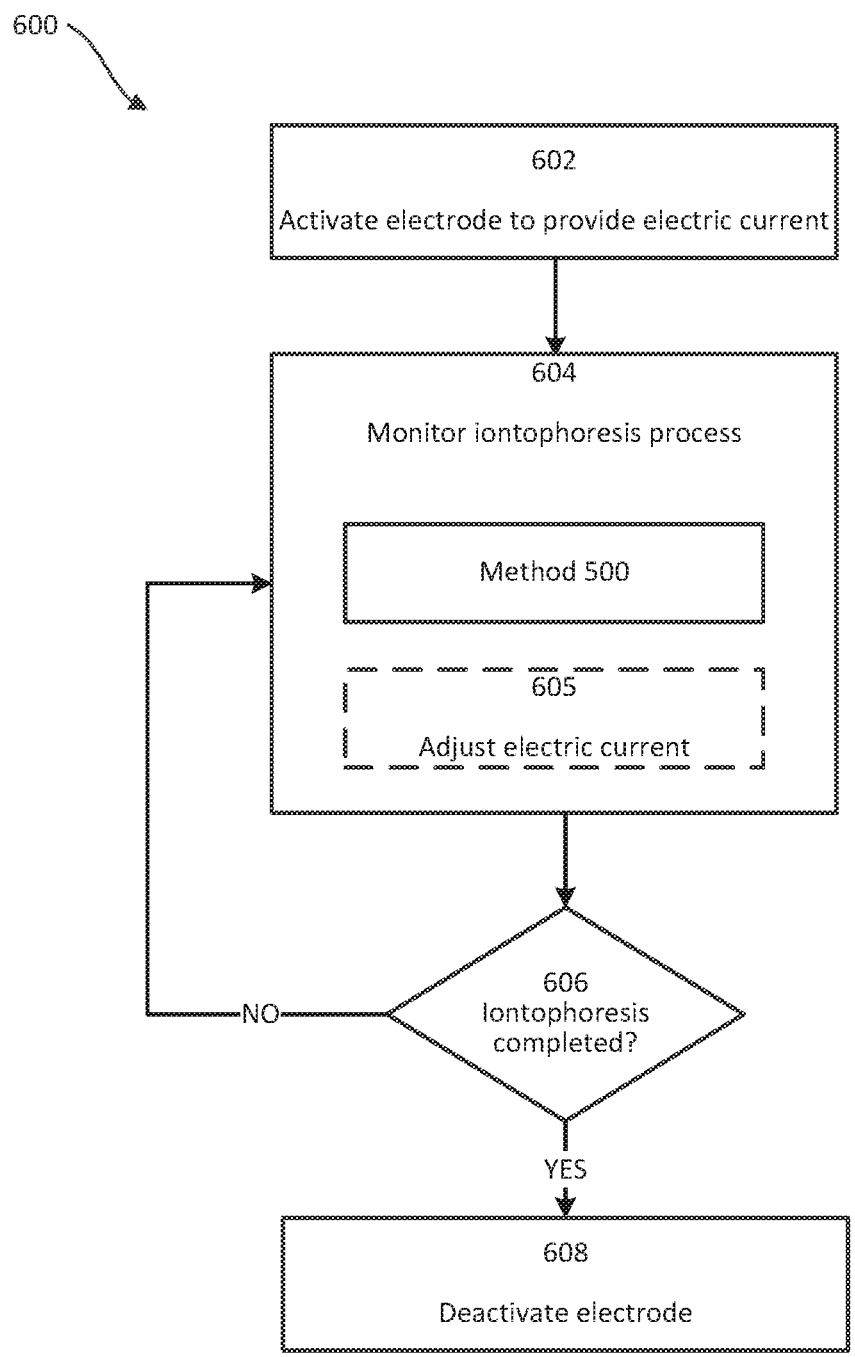
FIG. 8 is a flow diagram illustrating a method of performing iontophoresis according to some embodiments.

FIG. 8 depicts a flow diagram of a method 600 of performing iontophoresis with a visualization system, such as any of the visualization systems described herein. An iontophoresis device (e.g., iontophoresis device 180 or 280) can be positioned within an ear of a subject. The iontophoresis device can fill the ear with an iontophoresis drug solution, such as, for example, a drug solution containing an anesthetic. The visualization system can be coupled to the iontophoresis system and, at 602, activate an electrode (e.g., electrode 184 or 284) of the iontophoresis device to deliver an electric current to the iontophoresis solution. The visualization system can include a button, switch, or other actuation mechanism that can be actuated to activate the electrode. In some embodiments, the visualization system can include a display (e.g., displays 172, 154, 254, or 372) that can display one or more graphical user interface elements (e.g., buttons, scales, bars, panels) that can be manipulated by a physician to activate and control delivery of electric current.

After activation of the electrode, the visualization system can be used to monitor the iontophoresis process, at 604. Monitoring of the iontophoresis process can include method 500, whereby image(s) of ear canal EC and a target treatment region can be captured and displayed to a physician. The image(s) can be filtered to identify when the iontophoresis procedure may be completed. For example, delivery of an anesthesia or other drug may reduce blood flow to the target treatment area and therefore cause the tissue in that area (e.g., the tympanic membrane TM) to blanch. The visualization system can filter the image(s) of ear canal EC to highlight the blanching to assist the physician in determining when the iontophoresis process may be completed. In some embodiments, an ionic dye or other color contract component can also be used to enhance the color of the tissue for visualization by a physician.

While monitoring the iontophoresis process, the visualization system can optionally adjust the electric current that is delivered by the electrode. For example, the visualization system may stop the electric current if it detects a safety issue, such as an increase in temperature, pressure, or other conditions within ear canal EC. The visualization system can be connected to one or more sensors (e.g., light sensors, temperature sensors, pressure sensors, etc.) that are located on a guide device, a stylus, or the iontophoresis device, and determine, based on data received from the sensors, to deactivate the electrode and stop the electric current.

The visualization system can determine when the iontophoresis process has completed, at 606, e.g., by monitoring when the tissue has become blanched, or by prompting for and/or receiving from the physician an indication that the iontophoresis process has completed. The visualization system can continue to monitor the iontophoresis process, at 604, until the iontophoresis process has completed. At 608, when the iontophoresis process has completed, the visualization system can deactivate the electrode.

Figure 9A:
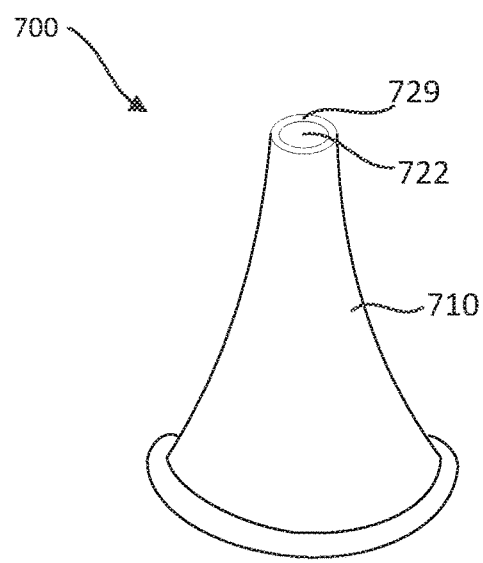
FIGS. 9A and 9B are perspective views of a speculum used in a visualization system according to some embodiments.
Figure 9B:
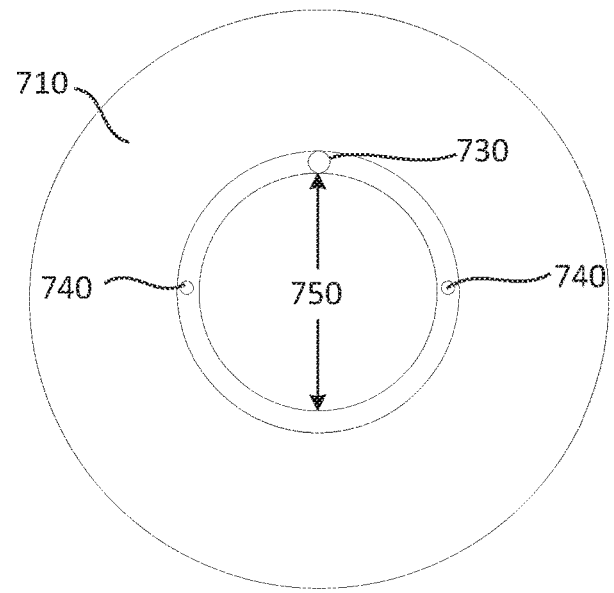

FIGS. 9A and 9B depict views of an example guide device, e.g., a speculum 700, that can form part of a visualization system, such as any of the visualization systems described herein. Speculum 700 includes a tapered body 710 that defines a lumen (not depicted) that ends in an opening 722 at a distal end 729 of speculum 700. Distal end 729 of speculum 700 can be inserted into an ear canal EC of a subject. Speculum 700 can come in a variety of sizes to ensure an anatomic fit between speculum 700 and ear canal EC. Lumen and opening 722 can be configured to receive an instrument (e.g., a tube delivery device) and to guide it into ear canal EC.

Speculum 700 includes one or more lights and/or light transmission elements 740. Lights 740 can be LEDs that are integrated and/or coupled to distal end 729 of speculum 700, as shown in FIG. 9B. When speculum 700 is inserted into ear canal EC, lights 740 can be activated to provide light within ear canal EC. Speculum 700 also includes a sensor, such as, for example, a CMOS sensor 730. CMOS sensor 730 can function as a camera that can capture image data of a target treatment area when speculum 700 is inserted into ear canal EC. While CMOS sensor 730 is depicted as being round in shape, in other embodiments, CMOS sensor 730 can take on other shape profiles (e.g., a square shape).

Opening 722 can vary in size depending on the size of speculum 700. Opening 722 can be sufficiently sized to receive an instrument (e.g., a tube delivery device). In an embodiment, speculum 700 with a diameter of 4 mm can have an opening 722 with at least a diameter 750 of 2.5 mm when CMOS sensor 730 has a diameter of approximately 1 mm and lights 740 have a diameter of approximately 0.5 mm.

Figure 10A:
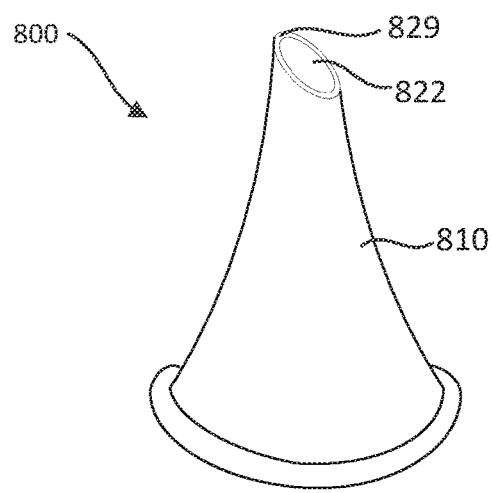
FIGS. 10A and 10B are perspective views of a speculum used in a visualization system according to some embodiments.
Figure 10B:
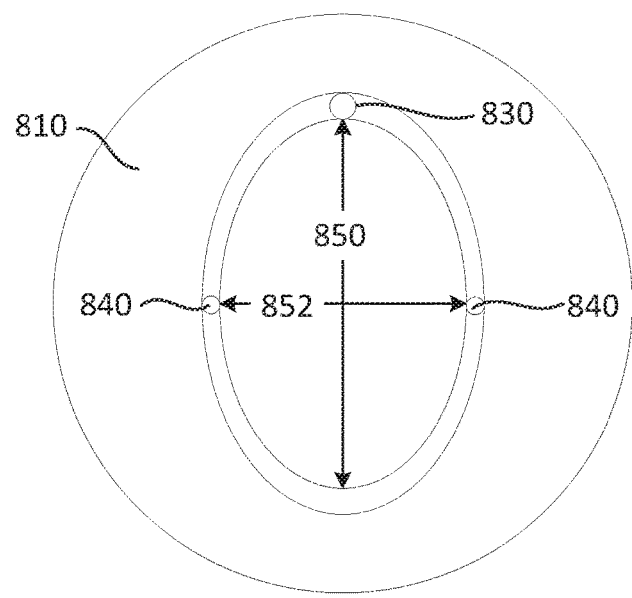

The opening available for an instrument can be increased (e.g., larger than 2.5 mm on a 4 mm speculum) if the distal end of the speculum is terminated at an oblique angle, such as is shown in FIGS. 10A and 10B. FIGS. 10A and 10B depict another example of a guide device, e.g., a speculum 800, that can be used with a visualization system, such as any of the visualization systems described herein. Speculum 800 includes a tapered body 810 that defines a lumen (not depicted) that ends in an opening 822 at a distal end 829 of speculum 800. Opening 822 can be formed at an oblique angle. Due to the tapering shape of speculum 800, the oblique arrangement of opening 822 can provide additional clearance for an instrument as compared to opening 722 of speculum 700. In particular, opening 822 can have a major diameter 850 and a minor diameter 852 that are greater than diameter 750 of opening 722.

Similar to speculum 700, speculum 800 also includes a CMOS sensor 830 and one or more lights and/or light transmission elements 840.

Figure 11:
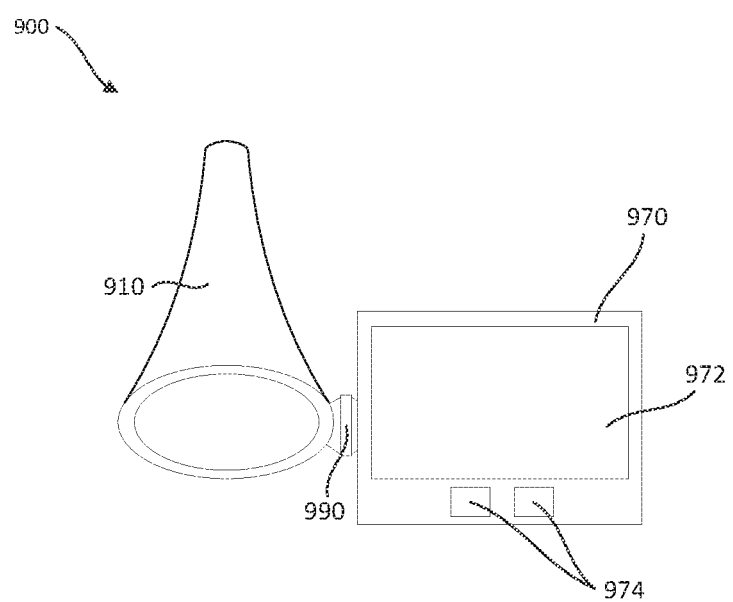
FIG. 11 depicts a speculum with an attached display used in a visualization system according to some embodiments.

FIG. 11 schematically depicts another example of a guide device, e.g., a speculum 900, that can form a part of a visualization system, such as any of the visualization systems disclosed herein. Speculum 900 includes a tapered body 910 that can form a lumen or channel (not depicted) for receiving and guiding an instrument into an ear canal EC. Body 910 can be releasably coupled via a connector 990 to a controller 970 with a display 972. Controller 970 can be similar to controllers 170 or 370, and can be configured to receive image data from one or more sensors disposed on speculum 900, and to display images of a target treatment area within ear canal EC on display 972. Controller 970 also includes one or more buttons 974, which can be actuated to change elements displayed on display 972 (e.g., adjust a brightness or color settings of display) and/or activate an iontophoresis device (not depicted) that can be connected to controller 970.

As shown, display 972 is adjacent to body 910 such that display 972 can be within the same field of view as an ear of a subject when body 910 is inserted into the ear. Connector 990 can include a hinge or ball joint that allows the physician to adjust an angle of display 972 to improve his view of display 972 before, during, or after an otologic procedure. Connector 990 can also allow the physician to rotate the speculum 900 relative to the controller 970. In some embodiments, connector 990 can enable coupling and/or decoupling (e.g., quick connect and disconnect) of speculum 900 from controller 970 and display 972 such that speculum 900 can be replaced with a different speculum having a different size and/or different sensor and light transmission elements.

Figure 12:
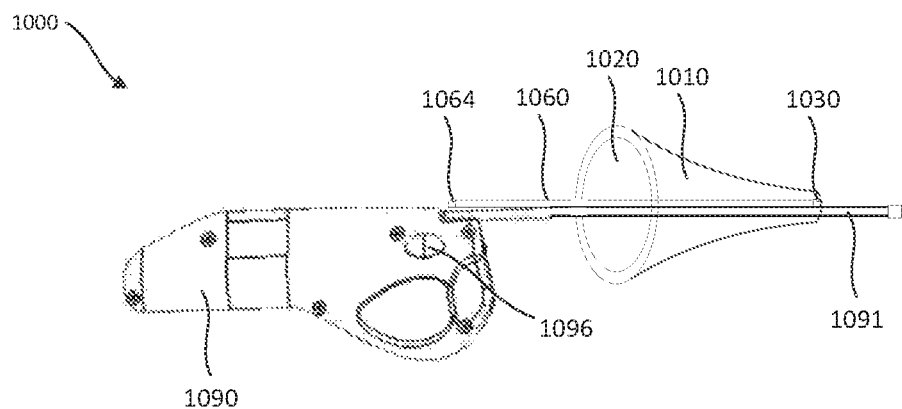
FIG. 12 depicts a stylus used in a visualization system with a speculum and a tube delivery device according to some embodiments.

FIG. 12 depicts an example of a stylus 1060 that can form a part of a visualization system, such as any of the visualization systems disclosed herein. Stylus 1060 can be used with a speculum 1010 that can include one or more light sources and/or transmit light from one or more remote light sources to an ear canal EC. Stylus 1060 can be removably coupleable to a shaft 1091 of a tube delivery device 1090, e.g., via an adhesive, a mechanical connection, and/or a magnetic connection. Stylus 1060 includes a sensor 1030 that can capture image data, and a wireless transmitter 1064 that can transmit the image data to a compute device (not depicted). Therefore, when stylus is coupled to tube delivery device 1090 and inserted into ear canal EC through a lumen or channel 1020 defined by speculum 1010, stylus 1060 can capture image data of ear canal EC and wirelessly transmit the image data to a compute device for processing and displaying. Tube delivery device 1090 can be activated via a button 1096 to deliver a tympanostomy tube into a tympanic membrane TM.

Figure 13:
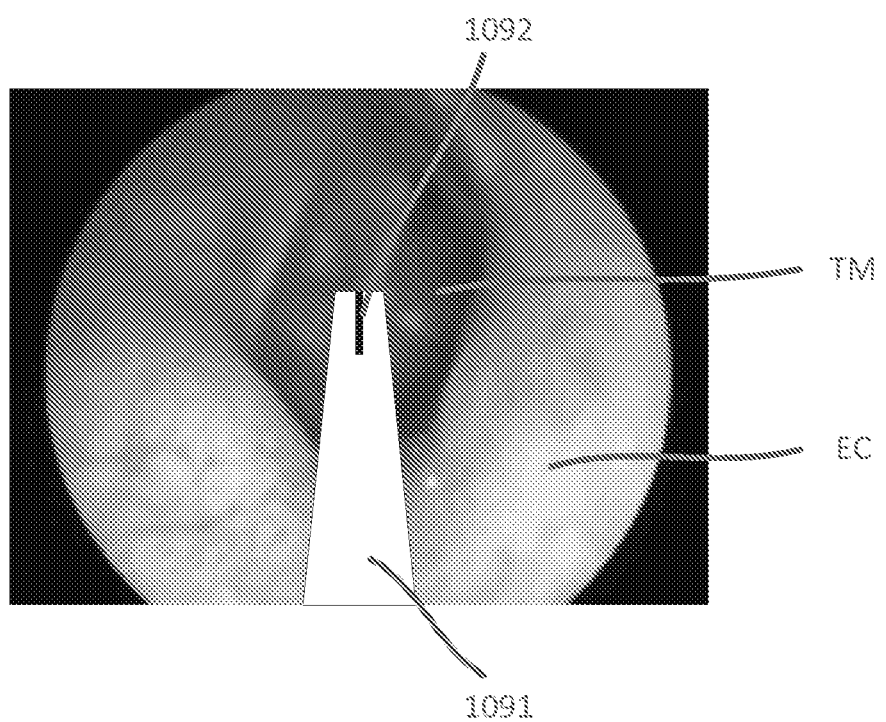
FIG. 13 depicts a view of an ear canal of a subject taken from a point of view of the stylus depicted in FIG. 12.

Stylus 1060 can be, for example, cylindrically shaped and have a diameter of approximate 1.5 mm. When coupled to tube delivery device 1090, a distal end of stylus 1060 can terminate before a distal end of shaft 1091 such that a view of an end of shaft 1091 can be seen in images captured via stylus 1060, such as is shown in FIG. 13. FIG. 13 depicts an example view of ear canal EC captured via stylus 1060. In some embodiments, such as the embodiment depicted in FIG. 13, shaft 1091 of tube delivery device 1090 can include a marking 1092 to help identify an end of shaft 1091 with the anatomy of the ear.

Figure 14:
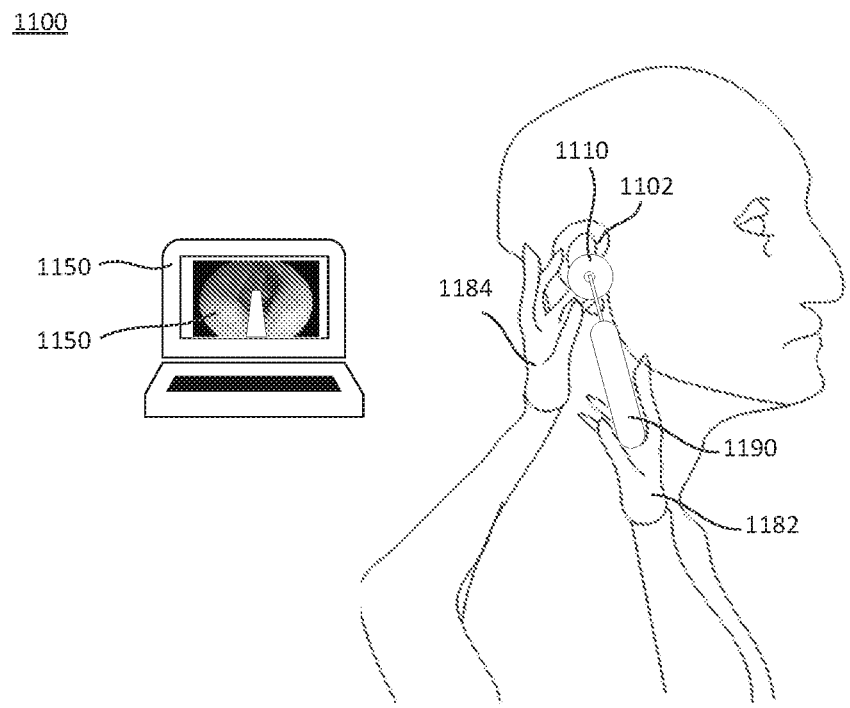
FIG. 14 is a schematic illustration of a view of a physician, including a visualization system, according to some embodiments.

FIG. 14 schematically illustrates a field of view 1100 from a point of view of a physician during an otologic procedure. As shown in the field of view 1100, a physician can view his hands 1182 and 1184, an external ear 1102, and an in-ear view 1151 of an inside of the ear provided by a visualization system. The visualization system includes a speculum 1110 that can be inserted into the ear. The speculum 1110 can include a sensor or imaging device (e.g., a camera) that can capture image data of the ear and send the image data to a compute device 1150 for display to the physician. By positioning the compute device 1150 near the patient, the physician can view his hands 1182 and 1184, the external ear 1102, and the in-ear view 1151 provided by the visualization system in a single field of view 1100. The physician, with one hand 1184, can hold the speculum 1110, and with his other hand, can hold an instrument 1190. The visualization system can allow the physician to manipulate the instrument without being restricted by his line-of-sight to the ear.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. An apparatus, comprising:
    a speculum having a proximal end and a distal end and defining a lumen;
    a light source configured to provide incident light to a target area disposed distal to the distal end of the speculum;
    a sensor configured to capture reflected light from the target area and generate image data based on the reflected light;
    a display configured to display an image of the target area based on the image data, the display coupled to the proximal end of the speculum such that the display is within a field of view of a user; and
    a tube delivery device extending through the lumen of the speculum to enable a distal end of the tube delivery device that extends beyond the distal end of the speculum into the target area to be viewed by the user while positioning the instrument.

2. The apparatus of claim 1, wherein the sensor is a complementary metal oxide semiconductor (CMOS) sensor.

3. The apparatus of claim 1, wherein the light source is configured to provide the incident light to the target area via one or more optical fibers.

4. The apparatus of claim 1, further comprising a lens integrated with the sensor and configured to focus the reflected light from the target area.

5. The apparatus of claim 1, further comprising an optical fiber configured to transmit the reflected light from the distal end of the speculum to the sensor.

6. The apparatus of claim 1, wherein the light source is a light-emitting diode.

7. The apparatus of claim 1, further comprising a coupling element that couples the display to the proximal end of the speculum and enables movement of the display along or about at least one axis.

8. The apparatus of claim 7, wherein the coupling element rotatably couples the display to the proximal end of the speculum such that an angle of the display relative to the speculum can be adjusted.

9. The apparatus of claim 7, wherein the coupling element couples the display to the proximal end of the speculum such that the display is radially offset from a longitudinal axis of the speculum.

10. The apparatus of claim 1, further comprising a processor configured to filter the image data such that a physical condition of the target area can be viewed in the image of the target area.

11. The apparatus of claim 1, further comprising a processor configured to reduce the incident light provided by the light source in response to detecting light saturation within the image data.

12. The apparatus of claim 1, further comprising a processor configured to cause the display to overlay visual guiding elements on the image of the target area, the visual guiding elements identifying one or more areas of interest.

13. The apparatus of claim 1, wherein at least one of the sensor or the light source is configured to rotate to adjust a view of the target area, and the processor is further configured to cause the display to rotate the image of the target area based on a rotation of the at least one sensor or the light source.

14. A system, comprising: a guide device having a proximal end and a distal end and defining a lumen; a light source configured to provide incident light to a target area beyond the distal end; a stylus including a sensor configured to capture reflected light from the target area and generate image data based on the reflected light, the stylus releasably engageable with the guide device; a tube delivery device inserted through the lumen into the target area; a processor configured to process the image data to produce an image of the target area and of a distal end of the tube delivery device located within the target area; and a display configured to display an image of the target area based on the image data.

15. The apparatus of claim 14, wherein the sensor is disposed at a distal end of the stylus.

16. The apparatus of claim 14, wherein the sensor is disposed at a proximal end of the stylus, the stylus further including an optical fiber configured to transmit the reflected light from a distal end of the stylus to the proximal end of the stylus.

17. The apparatus of claim 14, wherein the stylus is configured to be mechanically coupled to the guide device.

18. The apparatus of claim 14, wherein the stylus has at least a distal end having a diameter of approximately 1.5 mm to 3 mm.

19. A method, comprising:
    positioning a distal end of a guide device in an ear canal of a subject, the guide device defining a lumen;
    illuminating, using a light source, a target area distal to the distal end of the guide device;
    inserting a distal end of an instrument through the lumen, beyond the distal end of the guide device, and into the target area;
    capturing, using a sensor releasably coupled to the guide device, reflected light from the target area; and
    displaying, using a display coupled to a proximal end of the guide device, an image of the target area and the distal end of the instrument within the target area, such that the image is within a field of view of a user while the user has inserted the instrument through the lumen of the guide device.

20. The method of claim 19, further comprising coupling a stylus including the sensor to the guide device such that the sensor can capture the reflected light while the instrument is being inserted through the lumen of the guide device.

* * * * *